(12) United States Patent
Warner et al.

(10) Patent No.: US 10,806,503 B2
(45) Date of Patent: Oct. 20, 2020

(54) METHODS AND SYSTEMS FOR ELECTROPHYSIOLOGY ABLATION GAP ANALYSIS

(71) Applicant: General Electric Company, Schenectady, NY (US)

(72) Inventors: Adrian F. Warner, Delafield, WI (US); Daniel Richard Schneidewend, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 929 days.

(21) Appl. No.: 15/425,104

(22) Filed: Feb. 6, 2017

(65) Prior Publication Data

US 2018/0221075 A1 Aug. 9, 2018

(51) Int. Cl.
*A61B 18/12* (2006.01)
*A61B 5/00* (2006.01)
(Continued)

(52) U.S. Cl.
CPC ............ *A61B 18/12* (2013.01); *A61B 5/4848* (2013.01); *A61B 2017/00199* (2013.01);
(Continued)

(58) Field of Classification Search
CPC .......... A61B 18/12; A61B 2018/00577; A61B 2018/00642; A61B 2018/00648;
(Continued)

(56) References Cited

U.S. PATENT DOCUMENTS

| 8,702,688 B2 | 4/2014 | Melsky | |
| 2007/0185485 A1* | 8/2007 | Hauck | A61B 34/20 606/41 |

(Continued)

FOREIGN PATENT DOCUMENTS

| EP | 2248480 A1 | 11/2010 |
| WO | 2012092275 A1 | 7/2012 |
| WO | 2015073871 A2 | 5/2015 |

OTHER PUBLICATIONS

"Catheter Ablation," UCSF Medical Center, Available Online at www.ucsfhealth.org/treatments/catheter_ablation/, as Updated Oct. 29, 2010, 1 page.

"FAQ: Electrophysiology Study and Catheter Ablation," UCSF Medical Center, Available Online at https://www.ucsfhealth.org/education/electrophysiology_study_and_catheter_ablation, as Updated Jan. 20, 2011, 2 pages.

(Continued)

*Primary Examiner* — Michael F Peffley
*Assistant Examiner* — Khadijeh A Vahdat

(57) ABSTRACT

A method of identifying gaps between electrophysiology (EP) ablation points may comprise: obtaining a plurality of ablation points recorded from a completed electrophysiology ablation procedure; digitally mapping the plurality of ablation points to an anatomical model corresponding to the completed electrophysiology ablation procedure; calculating ablation gap probability distributions for each of the plurality of ablation points based on ablation tolerance variables associated with each of the plurality of ablation points; and overlaying the ablation gap probability distributions on to the digitally mapped plurality of ablation points on the anatomical model. In this way, ablation gaps may be non-invasively identified prior to patient discharge, thereby allowing for further EP treatment to remove the ablation gaps while reducing readmission rates. Furthermore, by representing ablation points using calculated ablation burn density distributions and ablation gap probabilities, the accuracy of identifying ablation gaps may be increased.

18 Claims, 7 Drawing Sheets

(51) Int. Cl.
    *A61B 18/00*     (2006.01)
    *A61B 17/00*     (2006.01)
    *A61B 34/10*     (2016.01)

(52) U.S. Cl.
    CPC ............ *A61B 2018/00577* (2013.01); *A61B 2018/00642* (2013.01); *A61B 2018/00648* (2013.01); *A61B 2018/00666* (2013.01); *A61B 2018/00702* (2013.01); *A61B 2018/00779* (2013.01); *A61B 2018/00797* (2013.01); *A61B 2018/00839* (2013.01); *A61B 2018/00875* (2013.01); *A61B 2034/105* (2016.02)

(58) Field of Classification Search
    CPC ........... A61B 2018/00666; A61B 2018/00702; A61B 2018/00779; A61B 2018/00797; A61B 2018/00839; A61B 2018/00875; A61B 2017/00199; A61B 2034/105; A61B 5/4848
    See application file for complete search history.

(56) References Cited

U.S. PATENT DOCUMENTS

2012/0004547 A1* 1/2012 Harks ............... A61B 8/486
                                                    600/439
2014/0221993 A1   8/2014 Bertolero et al.

OTHER PUBLICATIONS

"Electrophysiology Procedure," UCSF Medical Center, Available Online at https://www.ucsfhealth.org/education/electrophysiology_procedure/, Available as Early as Nov. 16, 2012, 2 pages.
"Cardiac ablation procedures," MedlinePlus Medical Encyclopedia, Available Online at https://medlineplus.gov/ency/article/007368.htm, as Updated Oct. 26, 2014, 4 pages.
Koutalas, E. et al., "Contemporary Mapping Techniques of Complex Cardiac Arrhythmias—Identifying and Modifying the Arrhythmogenic Substrate," Arrhythmia & Electrophysiology Review, vol. 4, No. 1, May 2015, Published Online Jan. 12, 2015, 9 pages.

* cited by examiner

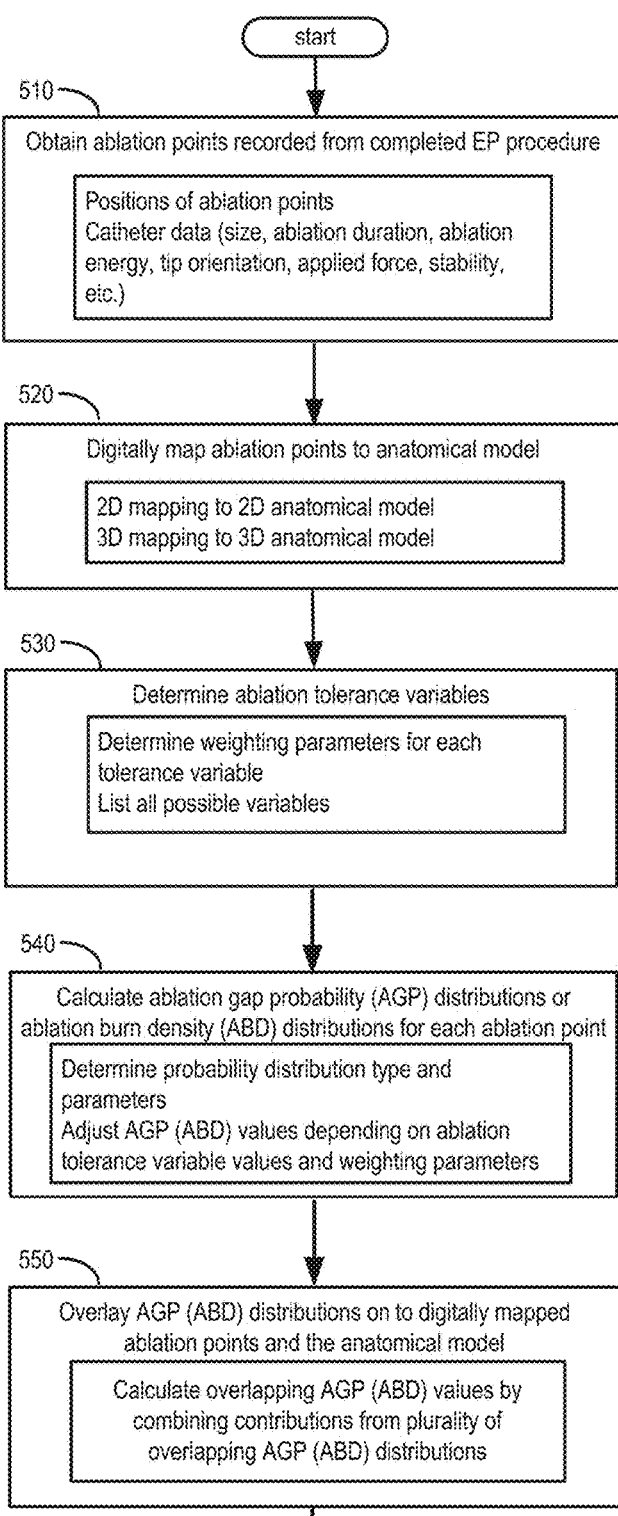
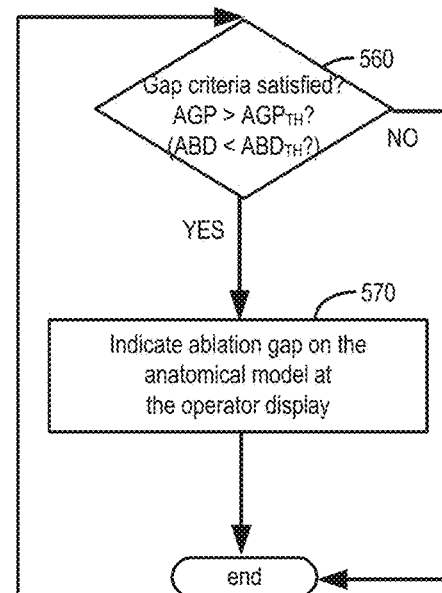
FIG. 5

METHODS AND SYSTEMS FOR ELECTROPHYSIOLOGY ABLATION GAP ANALYSIS

FIELD

Embodiments of the subject matter disclosed herein relate to a methods and systems for conducting electrophysiology ablation.

BACKGROUND

Electrophysiology (EP) ablation is an invasive surgical procedure for treating conditions such as cardiac arrhythmia including, but not limited to, atrial fibrillation. Small and flexible catheters conveying electrodes and various instruments are inserted into blood vessels in a patient's body and guided toward the target tissue or organ to be treated. In the case of cardiac ablation, electrodes are guided through the catheters to the heart to measure and diagnose the heart condition, and to identify the tissue causing the arrhythmia. Once the problematic tissue is identified, electrical radiofrequency energy (or other types of energy) are delivered to the heart by way of the catheter to destroy the tissue, thereby blocking and disrupting the electrical pathways responsible for the arrhythmia. EP ablation procedures may also be used in other areas of the body; for example, renal denervation involves guiding electrodes to the renal artery, and ablating tissue therein to reduce hypertension. EP ablation may also be used for treating arthritis, neck pain, and back pain. Due to inherent uncertainties associated with factors including catheter positioning, energy delivery, and tissue morphology, the EP tissue ablation treatment can often be inadequate, and residual propagation of the electrical pathways causing the arrhythmia can subsist. For example, a gap may arise within and disrupt a linear ablation lesion during pulmonary vein isolation or a gap may be left in a precision burn for treatment of an arrhythmic rotor. Errors in gap identification can result in a change in the conduction pathway after EP ablation, but without elimination of the underlying condition (e.g. arrhythmia). Consequently, a relatively high percentage of ablation cases regularly involve patient readmission for follow-up EP ablation procedures, thereby increasing healthcare costs, increasing patient health complication risks, and reducing patient satisfaction. Furthermore, due to the propensity of follow-up procedures, EP ablation's utility as a permanent cure for cardiac arrhythmia (and other conditions) is limited; instead, patients often rely on EP ablation for repeat treatment and management of their health conditions in order to mitigate risks of complications such as stroke, heart failure, and death, in the case of treating arrhythmia.

Melsky et al. (U.S. Pat. No. 8,702,688) describe a system for capturing still and live images of tissue ablation surgical sites by delivering an endoscope and camera to the ablation sites by way of a catheter. The live and still images are used to analyze the sufficiency of the lesions where tissue ablation has been performed. Mercader et al. (WO 2015/073871) is related to a system for imaging heart tissue including a catheter with an optical fiber for illuminating tissue at the ablation lesion site to excite mitochondrial NADH, a camera for receiving the NADH fluorescence signal from the illuminated tissue, and a processor for analyzing the NADH fluorescence signal. The system captures NAHD fluorescence images across a 2D line of the lesion site to determine a depth of the lesion site based on the NAHD fluorescence.

The inventors herein have recognized various issues with the above approaches. Namely, these conventional approaches are invasive, delivering additional devices such as endoscopes and cameras into the patient's body during the EP ablation procedure, which significantly increase the complexity, cost, duration, and risk of complications associated with the EP ablation procedure. For example, additional catheters may need to be conveyed inside the patient's body in order to accommodate these devices, which can increase a risk of complications and lengthen the duration of the procedure. Furthermore, additional technology such as NADH excitation, fluorescence sensors, endoscopes, and signal processing thereof is used, raising equipment and capital costs for the procedure. Further still, additional training and experience associated with using the technology may be required for the treating physicians before the lesion site sufficiency can be reliably assessed, thereby increasing physician-to-physician variability. Further still, factors such as tissue topography, movement of the tissue during the procedure, physician experience, and other sources of uncertainty in the ablation system are not accounted for, thereby reducing a reliability of correctly identifying EP ablation location which may result in gaps and lesion site deficiencies.

BRIEF DESCRIPTION

In one embodiment, the issues described above may be at least partially addressed by a method of identifying gaps between electrophysiology (EP) ablation points, comprising: obtaining a plurality of ablation points recorded from a completed electrophysiology ablation procedure; digitally mapping the plurality of ablation points to an anatomical model corresponding to the completed electrophysiology ablation procedure; calculating ablation gap probability distributions for each of the plurality of ablation points based on ablation tolerance variables associated with each of the plurality of ablation points; and overlaying the ablation gap probability distributions on to the digitally mapped plurality of ablation points on the anatomical model.

In another embodiment, a method of identifying gaps between electrophysiology ablation points may comprise: obtaining a plurality of ablation points recorded from a completed electrophysiology ablation procedure; digitally mapping the plurality of ablation points on to an anatomical model corresponding to the completed electrophysiology ablation procedure; calculating ablation burn probability distributions for each of the plurality of ablation points based on ablation tolerance variables associated with each of the plurality of ablation points; and overlaying the ablation burn probability distributions on to the digitally mapped plurality of ablation points on the anatomical model.

In another embodiment, an electrophysiology ablation system may comprise an operator display, and a controller electrically coupled to the operator display, the controller including executable instructions thereon to: obtain a plurality of ablation points recorded from a completed electrophysiology ablation procedure; digitally map the plurality of ablation points on to an anatomical model corresponding to the completed electrophysiology ablation procedure; calculate ablation gap probability distributions for each of the plurality of ablation points based on ablation tolerance variables associated with each of the plurality of ablation points; overlay the ablation gap probability distributions on to the digitally mapped plurality of ablation points on the anatomical model; and display the ablation gap probability distributions overlaid on to the digitally mapped plurality of ablation points on the anatomical model on the operator display.

For each of these embodiments, the resulting gap probability distributions and/or ablation burn probability distributions may be used by an operator (e.g., the physician) to locate and mitigate possible gap locations via additional ablation applications or diagnosis. In this way, the technical effect of predicting and identifying gaps between electrophysiology ablation points recorded from a completed electrophysiology ablation procedure may be more reliably and consistently achieved, thereby reducing readmission rate for follow-up EP ablation procedures. Further technical effects are listed as follows. For example, because invasively conveying additional instruments into the patient's body is precluded, the risk of complications and the duration of the EP ablation procedure may be reduced. Furthermore, additional equipment and technology costs associated with digital camera image processing, NADH fluorescence, and the like may be avoided. Further still, in the case where the ablation gap probability distributions (and/or the ablation burn probability distributions) account for the operator experience level, physician-to-physician variability associated with EP ablation can be reduced. Further still, the methods and systems for identifying gaps between EP ablation points may be easily and flexibly retrofitted to augment existing EP ablation systems. Further still, the ablation gap probability distributions (and/or the ablation burn probability distributions) may be easily and flexibly adjusted by the operator to account for a broad range of ablation tolerance variables, which can allow for a more reliably and accurate identification of gaps between EP ablation points. For example, in some cases, ablation tolerance variables can account for complexities in the tissue topography and real-time movement of the tissue during the EP ablation, thereby increasing a reliability of identifying gaps between EP ablation points.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 5 is an example flow chart for a method identifying gaps between ablation points.

DETAILED DESCRIPTION

The following description relates to various embodiments of methods and systems for conducting electrophysiology (EP) ablation.

In one embodiment, the issues described above may be at least partially addressed by a method of identifying gaps between electrophysiology ablation points, comprising: obtaining a plurality of ablation points recorded from a completed electrophysiology ablation procedure; digitally mapping the plurality of ablation points to an anatomical model corresponding to the completed electrophysiology ablation procedure; calculating ablation gap probability distributions for each of the plurality of ablation points based on ablation tolerance variables associated with each of the plurality of ablation points; and overlaying the ablation gap probability distributions on to the digitally mapped plurality of ablation points on the anatomical model.

Figure 1:
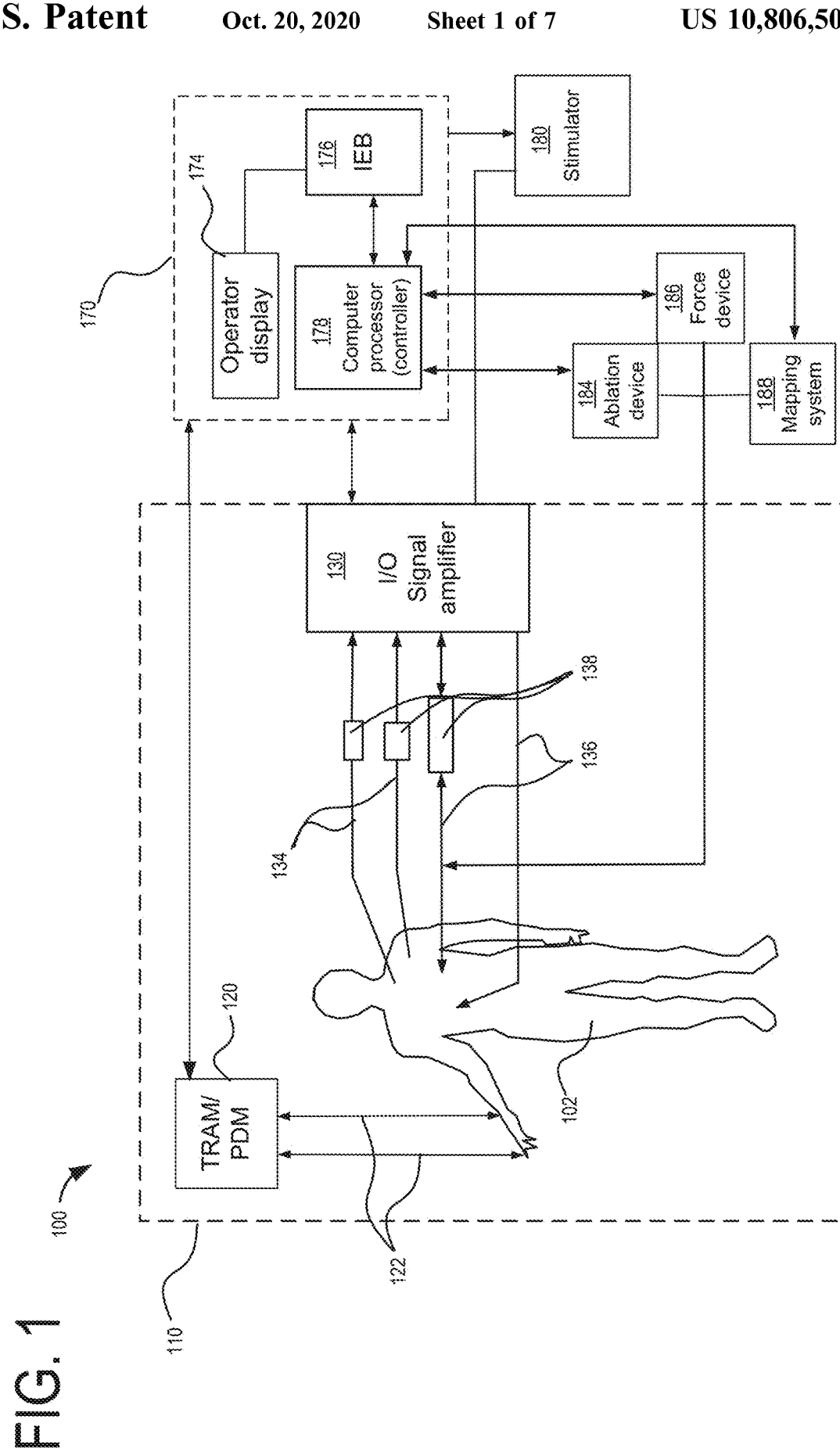
FIG. 1 is a schematic showing a block diagram of an example EP ablation system, including a controller and an operator display.
Figure 2:
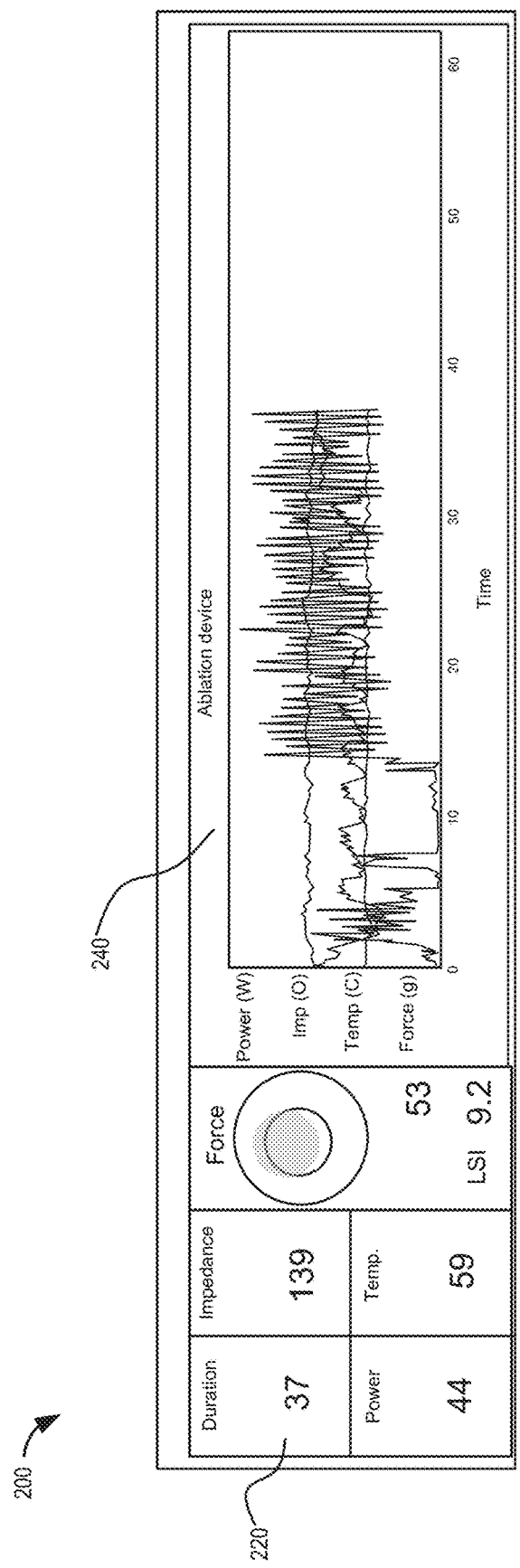
FIG. 2 is an example schematic of a screenshot from an operator display for an EP ablation system.

EP ablation involves delivering electrical energy by way of catheter electrodes to various tissue sites within a patient's body. The procedure may be monitored on an operator display and data associated with the ablation points may be recorded on a computer processor, as shown in FIG. 1. A screenshot from an operator display showing examples of recorded data associated with ablation points is illustrated in FIG. 2. The position of the ablation points can be overlaid on to an anatomical model, as shown for a conventional representation of ablation points in FIG. 3. Ablation gap probability distributions and/or ablation burn density distributions may be calculated by accounting for ablation tolerance variables and the recorded data associated with the ablation points. Gaps between EP ablation points can be identified from the ablation gap probability distributions and/or ablation burn density distributions, as visualized in FIGS. 4, 6, and 7. The ablation gap probability distributions and/or ablation burn density distributions may be represented by various statistical distributions, such as a Gaussian distribution, as shown in FIG. 8. A flow chart for a method of identifying the gaps between EP ablation points is shown in FIG. 5; the method may include executable instructions residing on board a controller or computer processor of FIG. 1.

Turning now to FIG. 1, it illustrates an example EP ablation system. During the an EP ablation procedure, various electrodes 134 may be invasively introduced into a patient's body 102 for monitoring and diagnosing conditions such as cardiac arrhythmia. Additionally, various catheters 136 for conveying various instruments, electrodes, and auxiliary input cables may be introduced into the patient's body 102. For example, ablation devices 184 may be conveyed by way of a catheter to direct electrical energy to destroy tissue. For example, in pulmonary vein isolation (PVI), the catheter directs the electrical energy to form electrical isolation lines isolating the tissue triggering atrial fibrillation. As a further example, force devices 186 may be introduced into the body for applying the catheter to the targeted lesion site for tissue ablation with a specified force. In one example, the force device 186 may include a strain gauge for measuring the force of the catheter applied to the target tissue site. The various catheters 136 including the devices conveyed therein, and the various electrodes 134 may be coupled to corresponding input modules 138, such as catheter input modules, for transmitting and receiving signals to and from the electrodes and cathode devices. The number of catheters and electrodes depicted in FIG. 1 are for exemplary and a larger number or smaller number of catheters and electrodes may be included.

The mapping system 188 may be included for generating a 2D and/or 3D structural view of the patient's anatomy as displayed on the operator display 174. Furthermore, the mapping system 188 may utilize 2D and/or 3D location methods for indicating a position of the ablation devices, catheters, and/or force devices within the patient's body. The position of the ablation devices, catheters, and/or force devices within the patient's body may be visually indicated on the operator display 174 for assisting in guiding the operator (e.g., physician) in conducting the EP ablation procedure. The data generated from the mapping system 188, including the position indication of the ablation devices, catheters, and/or force devices within the patient's body and the 2D/3D structural data of the patient's anatomy may be received as input by the computer processor 178. The computer processor 178 may process the data received from the mapping system, including performing statistical analyses, when evaluating gap probabilities between ablation lesions and when performing calculating ablation lesion probability distributions. The mapping system 188 may further receive feedback or input signals from computer processor 178 to assist in generating the 2D/3D structural view of the patient's anatomy. For example, the mapping system 188 may, in conjunction with the computer processor 178, may calculate inherent uncertainties or tolerances associated with the indicated positioning of the catheter, ablation, and/or force devices. The uncertainties, tolerances, and other calculated parameters may depend on the 2D/3D structural topography and morphology (and other ablation tolerance variables) of the patient's anatomy in the vicinities of the catheter, ablation, and/or force devices.

The input modules 138 may be further connected to an application module and input/output signal amplifier 130. The application module and signal amplifier 130 acquires patient data recorded from the EP ablation procedure such as surface electrocardiograms (ECGs), intracardiac signals, invasive blood pressure, and pacing activity. Pacing activity may comprise sending electrical signals to control (or pace) the heart rate in order to diagnose arrhythmia or other heart conditions. Non-invasive patient data such as non-invasive blood pressure and blood oxygen content ($SpO_2$) may also be recorded from electrodes 122. The electrodes 122 may transmit signals to a patient interface module 120, which serve as an intermediary for communicating to the computer processor (controller) 178 and the operator display 174. Examples of other invasive and non-invasive patient data which may be recorded include temperature, thermal dilution cardiac output, and respiration rate. The patient interface module 120 may also communicate with the application module and signal amplifier 130 by way of the controller 178. The patient interface module 120 and the application module and signal amplifier 130 may be connected to the controller by way of fiber optic cables so that the various recorded data signals may be simultaneously displayed at the operator display.

Figure 3:
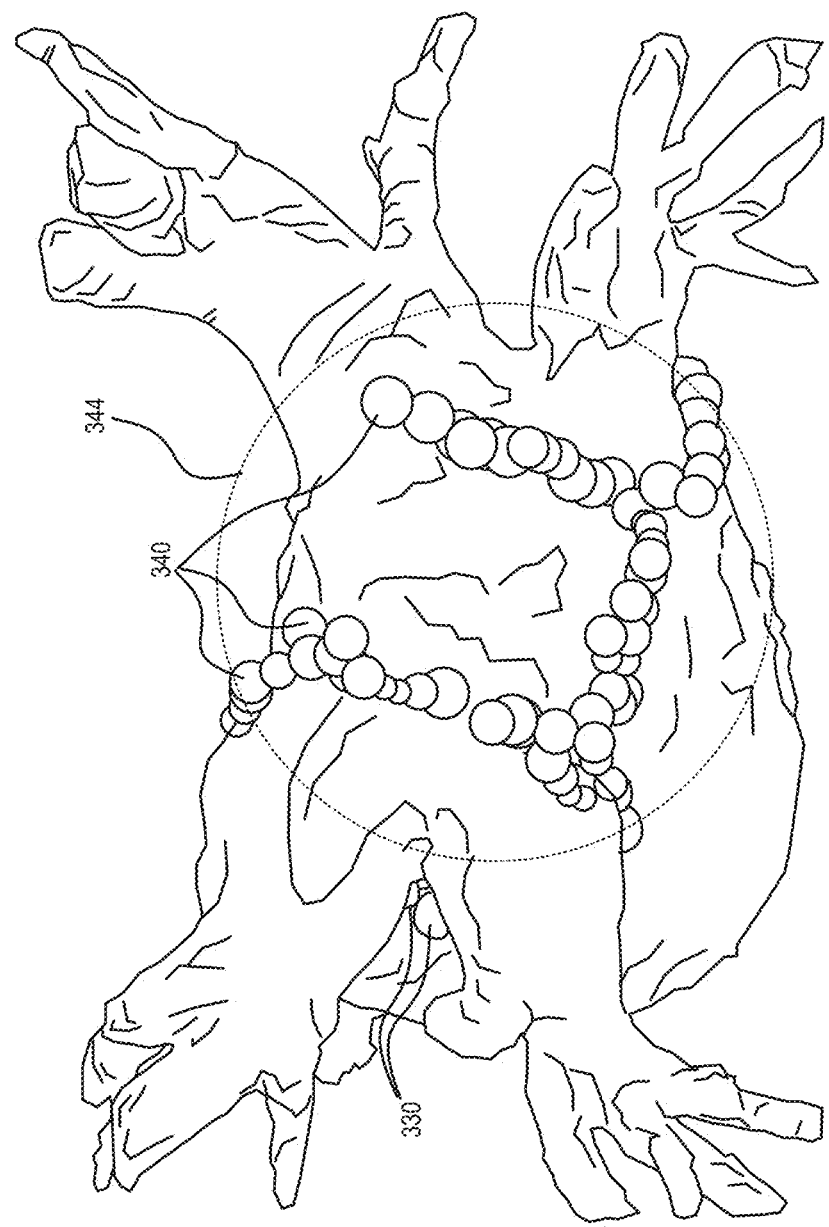
FIG. 3 is an example schematic showing lesion sites from an EP ablation procedure conventionally overlaid on to a digital anatomical model.

Operator display 174 may include a computer monitor for displaying and or receiving input (e.g., from a touch screen) from a user. For example, the operator display 174 may include two-dimensional (2D) and/or three-dimensional (3D) anatomical models of the tissue site being treated. For example, an anatomical model of the heart may be displayed, as shown in FIG. 3. The operator display may also output recorded data from a completed ablation procedure such as catheter-related data (e.g., catheter force, catheter-tissue contact angle, power and duration of ablation, and the like), and exemplified in FIG. 2. The operator display 174 may also display calculated data such as ablation gap probability and/or ablation burn density distributions associated with each ablation point, and these calculated data may be overlaid on the anatomical model.

Input devices (e.g., from a touch screen, mouse, keyboard or other input device) may also be coupled to the controller 178 for receiving input from a user. The controller 178 may include executable instructions thereon to receive recorded data from an EP ablation procedure, including recorded data related to the ablation points. Furthermore, the controller 178 may, in conjunction with the operator display 174, application module and signal amplifier 130, and patient interface module 120, receive operator input related to ablation tolerance input variables, which can be used to calculate the ablation gap probability distributions and/or ablation burn density distributions, and to identify and predict gaps between ablation points, as described further below with respect to FIG. 5. The operator input related to ablation tolerance input variables can include the relative weighting assigned to each ablation tolerance variable for determining their respective contributions to the ablation gap probability distributions and/or ablation burn density distributions. Gaps between ablation points may refer to any tissue that is insufficiently or incompletely treated by way of the completed EP ablation. If left untreated, gaps between ablation points may increase a risk of a patient being readmitted for further EP ablation treatment because electrical signals causing malfunctioning (e.g., atrial fibrillation or arrhythmia in cardiac EP ablation) may be partially blocked. Furthermore, the likelihood of readmission for EP ablation may increase because electrical signals responsible for tissue malfunctioning may be temporarily halted; following EP ablation, incomplete or insufficiently ablated tissue may heal and the electrical signals responsible for tissue malfunctioning may resume.

An integrated electronics box (IEB) 176 may provide power and distribute video signals to the operator display 174, applications module and signal amplifier 130, and the patient interface module 120. The IEB 176 may also house an uninterruptible power source (UPS) that functions as a backup battery and surge protection device for the EP ablation system. The IEB 176 may further supply power to any peripheral devices connected to the patient interface module 120 and the application module and signal amplifier 130. For example, the ablation device, force device, and any sensors for transmitting recorded data during the ablation procedure may be powered by the IEB 176. A stimulator module 180 may serve to actuate pacing and or other stimulation signals to electrodes in contact with the tissue sites. The stimulator signal may be input into the application module and signal amplifier 130 where a set of relays can route the signal to any of the catheter electrodes connected to the application module and signal amplifier 130.

Turning now to FIG. 2, it illustrates an example of a typical screenshot 200 from an operator display 174 displaying real-time data from an in-progress ablation procedure. The chart 220 shows numerical values of ablation procedure parameters such as the duration of the ablation, the ablation power, the impedance, temperature, force and lesion size index (LSI). Plot 240 displays real-time and historical trend lines of some of the parameters such as power, impedance, temperature, and catheter-tip tissue contact force. The ablation duration indicates how long the electrical energy is applied to deliver lesions at the tissue site. A longer ablation duration may indicate a larger and/or deeper lesion site than a shorter ablation duration. Similarly, higher power values indicate increased rates of energy delivered to the tissue site, and may indicate larger and/or deeper lesion sites. Impedance measurements at the catheter tip may also be used to provide a numerical indication of the extent of tissue ablation at the ablation site. However, impedance can be influenced by many factors such as catheter position, catheter tip size, catheter contact, and catheter temperature. When electrical energy (e.g., radio waves, ultrasonic energy, and the like) is delivered to the tissue site, heat is generated, burning the tissue. The catheter temperature can thus provide another indication of the extent of ablation at each ablation point.

Maintaining desired catheter tip-tissue contact force can aid in delivering robust ablation lesions. More robust catheter tip-tissue contact reduces dissipation of energy into the circulating blood pool surrounding the lesion site resulting in more robust energy coupling and delivery to the tissue. Maintaining a desired contact force during ablation procedures can be more difficult depending on the catheter type, lesion site location, and other factors. For example, irrigated tip catheters (irrigation with saline) may hinder accurate measurement or maintenance of a desired catheter tip-tissue contact force. Furthermore, if the lesion tissue site has a complex three-dimensional topography, maintaining catheter-tip tissue contact force may be more challenging. Catheter tip-tissue contact force may be indicated by the circular dot within the two-dimensional concentric circles. The size of the dot may represent the magnitude of the measured catheter tip-tissue contact force and the position of the dot with respect to the center of the concentric circles may indicate a measured catheter angle with respect to the tissue surface. The lesion size index (LSI) represents a unitless approximation that is roughly proportional to the size of the dead tissue resulting from the ablation. LSI may be a composite parameter that takes into account one or more of the ablation procedure parameters such as duration, impedance, power, and temperature. For example, LSI may be a composite value of an integrated product of force and power over time.

The display shown in FIG. 2 allows for an ablation operator to receive an overall summary of the progress of the ablation procedure at an ablation point. Based on the values of the ablation procedure parameters displayed, the operator can evaluate the sufficiency of individual ablation points (e.g., individual ablation lesion sites). However, single numerical values are deficient for quantifying, measuring, and predicting ablation burn density (e.g., ablation lesion density) and ablation gap probability distributions that can continuously vary in two or three dimensions in the tissue extending outward from an ablation point. For example, due to varying tissue resistivity, tissue morphology and tissue topology, the conduction and level of ablation energy may decrease as a distance from the ablation catheter tip contact point increases. Consequently, each ablation point may be more accurately represented as a distribution of ablation burn density, as indicated by the ablation points 420, 430, 440, and 450 illustrated in FIG. 4. Furthermore, although the information communicated from the display in FIG. 2 provides an indication of the sufficiency of an individual ablation point, there is no information associated with continuity of the ablation lesions, or gaps between the individual ablation points. For example, each ablation point may result in an area of burnt tissue radiating outward from the catheter tip-tissue contact point; however the ablation burn density of the burnt tissue may not be uniform. In particular, the ablation energy applied from the ablation device may be focused and more intense at the catheter-tip tissue contact point and less focused and less intense at distances further away from the catheter tip-tissue contact point. Further still, the distribution of the ablation burn density may vary with each ablation point, depending on the tissue topography and morphology at that ablation point, in addition to other ablation parameters (as described with reference to Table 1 below). For example, the ablation gap probability and the ablation burn density distributions of two ablation points may be unequal. As such, gaps between ablation points may also be more probable when ablation points are located farther apart, and when the ablation burn density values are lower. In this way, an ablation gap probability distribution may be used to indicate a likelihood of an ablation gap between two or more ablation points.

Turning now to FIG. 3, it illustrates a 3D digital anatomical model 300 of a left atrium of a heart 320. 3D digital anatomical models may be generated by a variety of methods, such as segmented computed tomography (CT), magnetic resonance (MR) imaging, rotational angiography, ultrasound exams, 3D mapping systems utilizing magnetic and/or electric spatial orientation, and the like. The anatomical model 300 may be constructed with respect to a 3D coordinate system, for example a 3D rectangular coordinate system 390. The ablation points 330 and 340 are overlaid on the 3D anatomical model corresponding to the locations of the ablation points, and are represented by a series of circles positioned across a region 344 of the left atrium of the heart targeted for pulmonary vein isolation (PVI). As shown, individual ablation points 340 are conventionally represented as homogeneous spheres centered about each ablation catheter tip-tissue contact location. Thus, the visualization of the ablation points 340 in FIG. 3 do not account for the distribution of ablation burn densities surrounding each catheter tip-tissue contact point. Furthermore, the homogeneous representation of the ablation points 340 fails to account for any distribution of ablation gap probabilities between the individual ablation points 340. Furthermore, the homogeneous representation of the ablation points 340 can misrepresent the tolerance and uncertainties associated with the lesion size, anatomical model, and mapping process.

In the case of a 3D anatomical model 300, as shown in FIG. 3, the ablation points 340 may be positioned and overlaid on to the model three-dimensionally. As such, uncertainty or tolerances associated with measured or calculated (or inferred) data recorded for each ablation point may depend on ablation tolerance variables such as tissue 3D topography and morphology, as further discussed below with reference to Table 1 and FIGS. 4-7. For example, if the 3D topography in the vicinity of the catheter tip-tissue contact point is uneven, it may be more difficult to maintain a consistent catheter tip-tissue contact force. Furthermore, the conduction of power through the tissue surrounding the ablation point may be uneven. Other ablation procedure parameters may similarly be impacted such that the ablation burn density distribution (and the ablation gap probability distribution) surrounding the catheter-tip tissue contact point may be highly uneven. As a further example, non-uniform if the tissue morphology is non-uniform ablation burn density distributions (and ablation gap probability distributions) surrounding the catheter-tip tissue contact point may be also be caused by irregular tissue morphology. For example, the density of the tissue surrounding the catheter tip-tissue contact point may vary, causing the propagation of the ablation burnt tissue radiating outward from the catheter tip-tissue contact point to be irregular and non-uniform. In some examples, denser tissue may be treated with higher amounts of energy before sufficient tissue ablation is reached relative to less dense tissue. In other examples, less dense tissue may conduct electrical energy at a lower rate than denser tissue and may be treated with higher levels of energy before sufficient tissue ablation is reached relative to denser tissue. Other factors such as tissue movement (pumping of the heart, circulation of blood or other fluids through the targeted tissue, and the like) can also influence the ablation burn density distributions (and ablation gap probability distributions) surrounding the catheter tip-tissue contact point because maintaining contact between the catheter tip and the tissue may be more difficult and conduction of electrical energy from the catheter tip to the tissue surface may be lower as compared to the case where the tissue is static (unmoving) during the ablation procedure.

Figure 4:
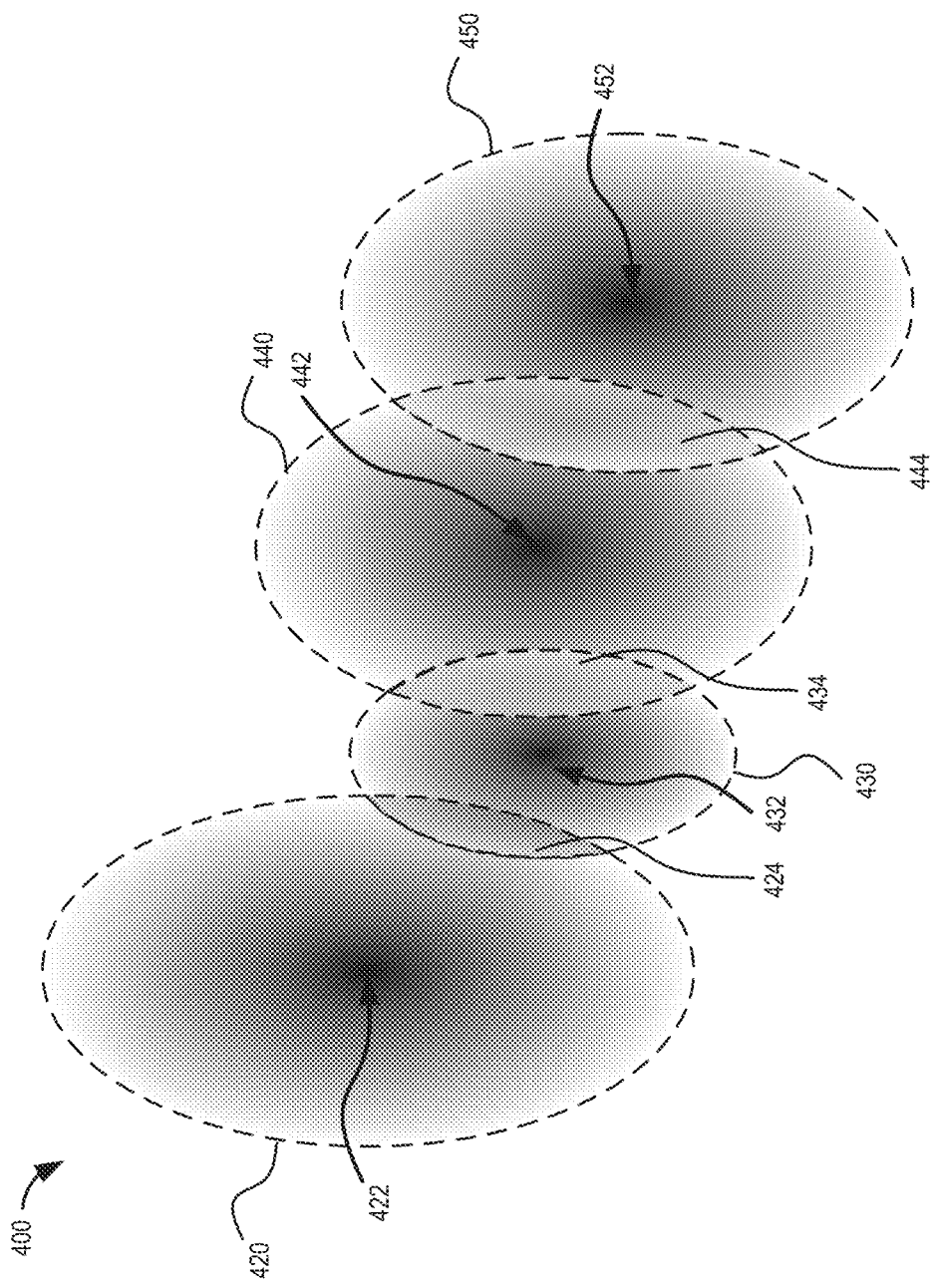
FIG. 4 is a schematic showing example methods for calculating gaps between EP ablation points.
Figure 6:
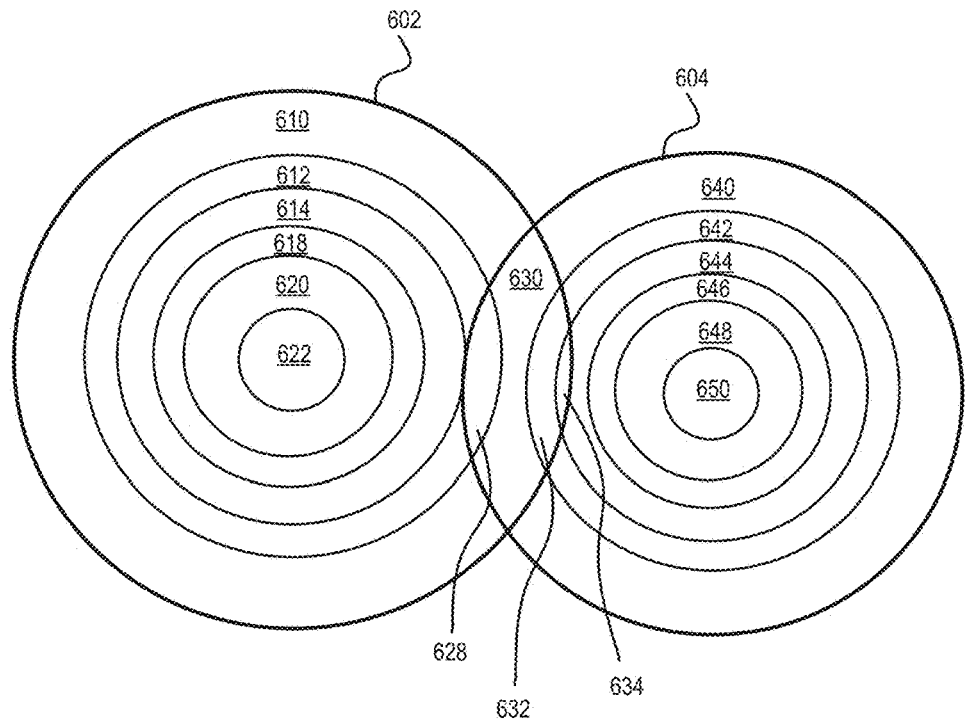
FIGS. 6 and 7 are schematics showing example methods for calculating gaps between EP ablation points.
Figure 7:
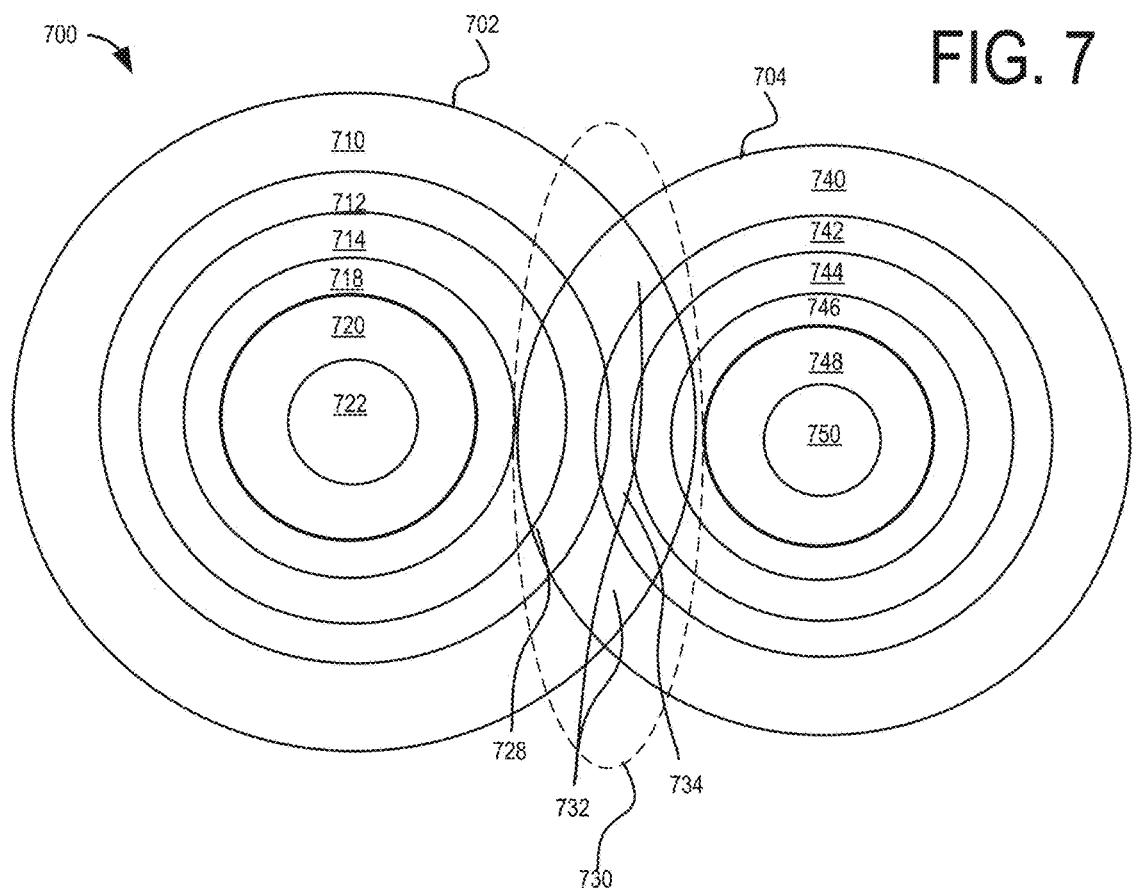
Figure 8:
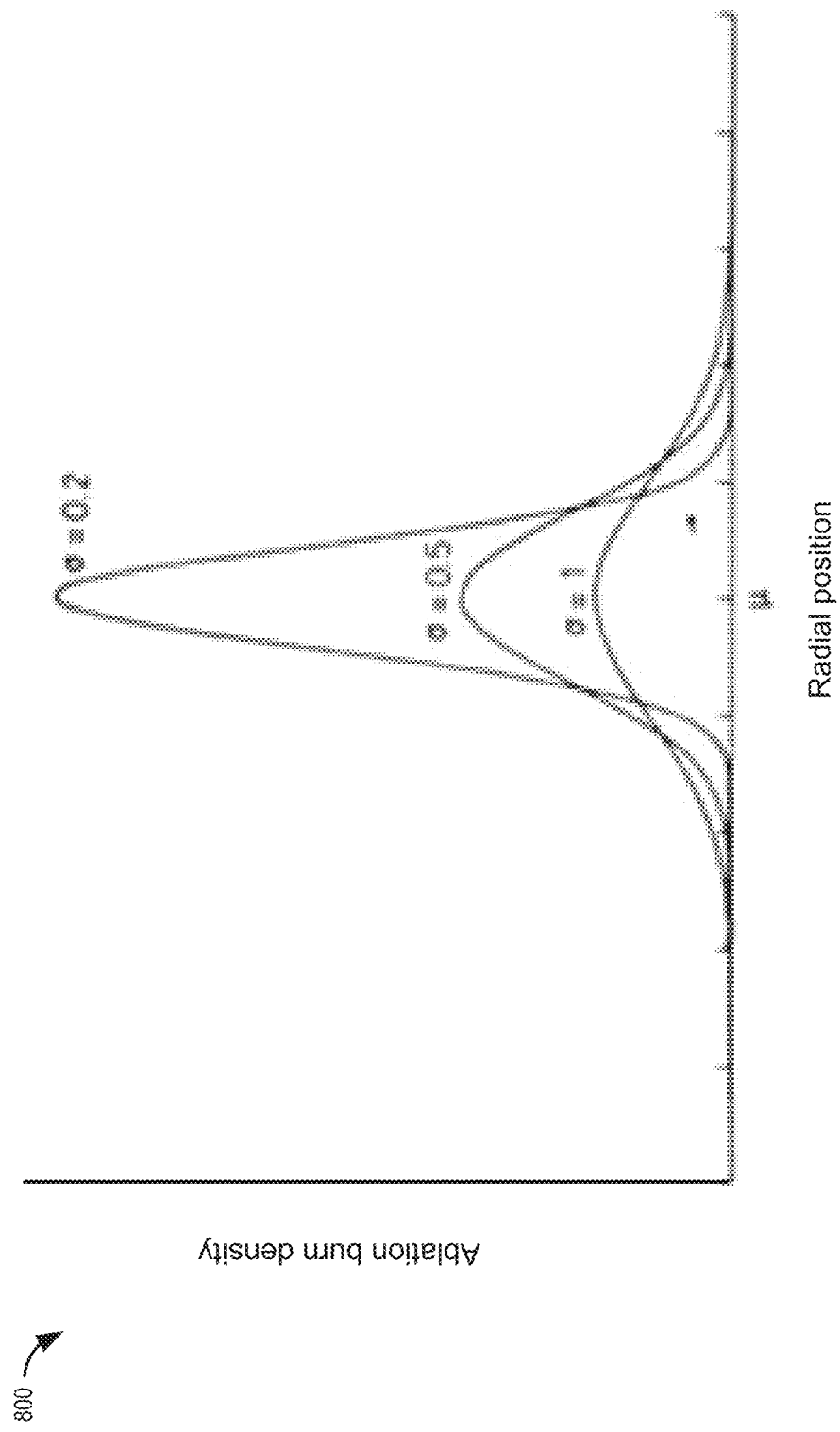
FIG. 8 is a plot illustrating a Gaussian distribution

Turning now to FIGS. 4, 6, and 7, they illustrate examples of methods for calculating, inferring, estimating, and/or predicting ablation gap probability distributions (and ablation burn density distributions) from recorded data and other operator-input (e.g., user-defined) data for a completed EP ablation procedure. FIG. 4 shows a schematic 400 of four adjacent ablation points 420, 430, 440, and 450. As an example, the ablation points 420, 430, 440, and 450 may represent a sequence of adjacent ablation points taken along a lesion line during pulmonary vein isolation. In contrast to the conventional ablation points 340 represented as homogeneous circles (or spheres) and overlaid on the 3D anatomical model in FIG. 3, the ablation points 420, 430, 440, and 450 are shown as shaded distributions of continuously varying density. In other words, each ablation point includes a concentric halos (in the case of 2D distributions) or spherical shells (in the case of 3D distributions) of ablation gap probabilities or ablation burn densities. The shaded distributions may be represented as 2D or 3D distributions, and may depend on the complexity of the distributions, the tissue topography, and the digital anatomical model used. The density of the shading can represent the ablation burn density distribution (in 2D or 3D) in the vicinity of each ablation point. The ablation points 420, 430, 440, and 450 are shown as having darker central regions 422, 432, 442, and 452, respectively, corresponding to regions of tissue located closest to the catheter tip-tissue contact point. As one example, the darker shading thereat may be due to the tissue receiving higher amounts of electrical energy, which can result in higher ablation burn densities. Farther away from the central regions 422, 432, 442, and 452, the ablation burn density distributions become lighter and lighter, corresponding to regions of tissue located farther and farther away, respectively, from the catheter tip-tissue contact point. As one example, the lighter shading may be due to the tissue receiving lower amounts of electrical energy, which can result in lower ablation burn densities. Representing ablation points as homogeneous ablation regions (e.g., ablation points 340 in FIG. 3) is insensitive to factors such as tissue density, conduction and dissipation of electrical energy from the catheter tip-tissue contact point, and other ablation tolerance variables (as further discussed below with reference to Table 1). Accordingly, representing ablation points as distributions (as shown in FIG. 4) rather than homogenous regions allows for more accurate determination of ablation burn density distributions and gaps between ablation points and regions where the ablation energy between ablation points is insufficient.

Ablation gap probabilities, the likelihood of finding tissue that has been insufficiently ablated so that electrical signals thereat are incompletely disrupted, may be inferred from the ablation burn density distributions and vice versa. For instance, ablation burn density distributions may have an inverse relationship with the ablation gap probability distribution. At higher ablation burn density values, the ablation gap probability is lower because there is a higher likelihood that tissue has been sufficiently ablated to disrupt electrical pathways therethrough. Similarly, at tissue locations corresponding to lower ablation burn densities, the ablation gap probability may be higher because there is a lower likelihood that tissue has been sufficiently ablated to disrupt electrical pathways therethrough. Referring to FIG. 4 again, the ablation points 420, 430, 440, and 450 may also represent shaded continuous ablation gap probability distributions. From the perspective of ablation gap probability distributions, the darker central regions 422, 432, 442, and 452, may correspond to tissue having lower ablation gap probabilities, being in closer proximity to the catheter tip-tissue contact point during the ablation. It then follows that the more lightly shaded areas more distal from the darker central regions 422, 432, 442, and 452, may correspond to tissue regions having higher ablation gap probabilities.

In some examples, the ablation burn density distribution (and the ablation gap probability distributions inferred therefrom) may be symmetrical and may represented by a plot 800 of a Gaussian statistical distribution (normal distribution) (FIG. 8). The Gaussian distribution is specified by two parameters: the mean value and the standard deviation (or variance). In some examples, the mean value, $\mu$, may coincide with the position of the catheter tip-tissue contact point. In other examples, the mean value, $\mu$, may not coincide with the position of the catheter tip-tissue contact point. The ablation burn density at the mean position value, $\mu$, may be higher, whereas at radial positions extending outward from $\mu$, the ablation burn density may decrease. The rate of decay in the ablation burn density distribution at radial positions extending further from $\mu$ may be determined by the standard deviation, a, of the distribution. The standard deviation describes the spread or width of the distribution. Several example Gaussian distribution curves having the same mean value, $\mu$, and different standard deviations, a, are shown in plot 800; as $\sigma$ increases, the distribution breadth broadens about the mean, whereas as $\sigma$ decreases, the distribution breadth narrows about the mean value.

In other examples, the ablation burn density distribution may be determined by other statistical distributions, such as a log-normal distribution, Weibull distribution. Various types statistical distributions may be applied to represent the ablation burn density distribution (and the ablation gap probability distributions inferred therefrom), and the type of statistical distribution may be selected depending on the EP ablation conditions. For example, an ablation system that pulses or modulates power in an on/off fashion may employ a binomial distribution to represent the ablation burn density distribution. Ablation burn density distributions for ablation systems employing linear power regulators may be represented by more uniform distributions. In another example, ablation burn density distributions for ablation systems employing closed loop control algorithms may be represented by exponential decaying distributions. For instance, as tissue conductivity decreases as it is ablated and dies, thereby inhibiting further ablation (because ablation energy penetration is reduced), and thus the ablation burn density distribution may decay exponentially as distance from the catheter tip contact point increases, and as time passes. The methods and systems described herein may allow for selecting and combining various types of statistical distributions to represent ablation burn density distributions. However, in many cases, the law of averages may have aggregate ablation burn density distributions tending toward being accurately represented by Gaussian distributions.

In any case, the values of the ablation burn density distribution are determined by specifying the parameters of the statistical distribution. For example, a skewed statistical distribution may be used to represent an ablation burn density distribution for the case where the catheter tip-tissue contact angle is not orthogonal; in these cases, the ablation energy may be directed primarily in the direction the catheter tip is pointing when it contacts the tissue surface, and as a result, the ablation burn density distribution may be non-symmetrical about the catheter tip-tissue contact point. For the case where the anatomical model is a 3D anatomical model, the ablation burn density distributions may be represented by 3D Gaussian distributions (or other 3D statistical distributions). In other words, the values of the ablation burn density distribution, as specified by the $\mu$ and $\sigma$, extend in three dimensions about the $\mu$. Furthermore, depending on the 3D symmetry of the ablation tolerance variables, one or more of the statistical distribution parameters describing the ablation burn density (and ablation gap probability) distribution may vary in one or more dimensions. For example, the standard deviation of a 3D Gaussian distribution may vary with an angle theta about the mean axis (for 3D using polar coordinates); in practical terms, this could correspond to the ablation site tissue topography (or other ablation tolerance variables) varying with theta about the mean axis, as an example.

The parameters of the ablation burn density distribution may be estimated, inferred, and/or calculated from a plurality of ablation tolerance variables. The ablation tolerance variables may quantify contributions to the overall ablation tolerance or uncertainty from certain factors. Sources of uncertainty can arise from the tolerance of the devices (e.g., catheter, ablation device precision limitations, and the like), system operators (e.g., physician surgical expertise level, fatigue, human error), the complexity of the system (e.g., tissue displacement or movement during surgery, irregular 3D tissue topography, heterogeneous tissue morphology), as well as other sources. Some non-limiting examples of ablation tolerance variables are shown in Table 1. Generally, as the uncertainty or variability in the ablation points described by the ablation tolerance variables increases, the estimated ablation burn density values may decrease, and the probability of ablation gaps between ablation points may increase. Furthermore, higher uncertainties in the ablation points may result in broad (e.g., higher standard deviation) ablation burn density and ablation gap probability distributions. In one embodiment, executable instructions on board an ablation system controller 178 may receive as inputs, a plurality of ablation tolerance variables corresponding to each ablation point; the controller 178 may then calculate ablation burn density distributions (and/or ablation gap probability distributions) corresponding to each ablation point based on the plurality of ablation tolerance variables. Other ablation tolerance variables, not listed in Table 1, may also be used as inputs by the controller 178 for calculating burn density distributions (and/or ablation gap probability distributions) at each ablation point.

TABLE 1

Examples of Ablation Tolerance Variables

| Variable type | Variable Examples | Description |
| --- | --- | --- |
| Tissue motion | Heart rate, blood flow, tissue motility, respiration rates | Factors describing movement of tissue during ablation. Increased motion may reduce accuracy of catheter tip force, position, and contact with tissue |
| Operator experience | Number of EP surgeries, years of experience, average readmission rate | Quantifies operating physician's experience with ablation procedure Increased operator experience may result in narrower ablation burn density distributions and/or increased ablation burn densities (and lower ablation gap probabilities) |
| Anatomical topography | Measure of topography irregularities (bumps, troughs, holes, protrusions, etc.) at the ablation site | Complex, irregular, non-smooth topography may reduce accuracy of catheter tip force, position, and contact with tissue, as well as conduction of electrical energy through tissue. |
| Anatomical morphology | Measure of tissue density variations (voids, liquids, solid tissue) in the ablation region; presence of scar tissue; tissue type (fat, muscle, organ) | Heterogeneities in the anatomical morphology may influence conduction of electrical energy through tissue, and result in more highly variable burn densities in the ablation region |
| Catheter | Catheter size, force, orientation, tip geometry | Uncertainties related to the catheter can reduce predicted ablation burn densities, and thereby increase predicted ablation gap probabilities |
| Ablation device | Power, duration, impedance, ablation technology type | Device tolerances due to electrode losses, tip losses, device uncertainty, ablation technology type |
| LSI | Dimensionless composite measure for predicting the size of an ablation lesion | Empirical measure |
| Jump Index | Dimensionless measure of catheter stability during ablation | Empirical measure |

TABLE 1-continued

Examples of Ablation Tolerance Variables

| Variable type | Variable Examples | Description |
| --- | --- | --- |
| Patient history | Age, health, readmission and EP surgery history | Complications in patient history may be associated with higher gap probabilities due to higher surgery complication risk |

Referring to Table 1, tissue motion ablation tolerance variables may include heart rate, pulse, blood flow, tissue motility, respiration rates, and other measures that may influence motion or time-varying attributes of the tissue at the ablation site during the EP ablation surgery. As examples: the pulsing of the heart while pumping blood may dilate and retract the tissue surface at the catheter tip, thereby introducing variability into the EP ablation quality; pulsing and flow of blood in the vicinity of or through the ablation site can impact conduction of electrical energy through the tissue; higher tissue motility can reduce precision in the catheter positioning and increase variability in the ablation. Operator experience ablation tolerance variables may include measures of a physician's expertise associated with performing the specific EP ablation procedure (e.g., cardiac ablation, renal denervation, ablation for treatment of neck pain, back pain, or arthritis): a lower readmission rate may indicate physician's skill associated with the likelihood of achieving a sufficient extent of ablation throughout the tissue region to disrupt electrical pathways causing a patient's condition; a higher number of completed EP surgeries or years of experience may indicate an decreased probability of gaps between ablation points. By accounting for operator experience in calculating ablation burn probabilities and ablation gap probabilities, operator to operator variability associated with EP ablation surgery and readmission rates can be reduced.

Anatomical topography ablation tolerance variables may provide a measure of topography irregularities (bumps, troughs, holes, protrusions, etc.) at the ablation site. For example, if the 3D topography in the vicinity of the catheter tip-tissue contact point is more complex (many bumps, troughs, protrusions), it may be more difficult to maintain a consistent catheter tip-tissue contact force. Furthermore, the conduction of power through the tissue surrounding the ablation point may be uneven. Further still, the anatomical model may be less precise in regions where the anatomical topography is more complex and it may be more difficult for the operator to accurately and precisely position the catheter at the lesion sites. In this way, more complex anatomical topography may lower ablation burn densities (increase ablation gap probabilities), which may prompt an operator to locate adjacent ablation points closer together in order to maintain a lower ablation gap probability.

Anatomical morphology ablation tolerance variables may provide a measure of tissue morphology variations in the ablation region. For example, tissue density may vary in three dimensions due to the presence of multiple phases such as voids, solid tissue, and fluids. Because the conductivity of electrical energy can vary depending on the tissue density, variability of the EP ablation can increase when tissue morphology is more complex. As one example, if the catheter tip is positioned at a tissue void, conduction of electrical energy from the catheter tip may be poor, giving rise to a higher ablation gap probability because the ablation burn density is lower. The presence of scar tissue (perhaps due to a prior EP ablation procedure) can also reduce conduction of electrical energy from the catheter tip, thereby increasing ablation gap probability. Variability in tissue types (e.g., fat, muscle, organ, and the like) can also increase uncertainty in the EP ablation procedure, giving rise to higher ablation gap probabilities.

Catheter ablation tolerance variables may include catheter tip size, applied force, tip orientation, and tip geometry. The catheter tip size and geometry may influence the precision with which the catheter tip can be positioned at the lesion site. For example, a larger catheter tip size may allow for a higher rate of electrical energy to be imparted to the tissue during the ablation. However, a higher uncertainty may be associated with positioning a larger catheter tip, especially if the tip dimensions are of the same order of magnitude as any tissue morphology features (e.g., troughs, protrusions, etc.) that may hinder contact between the catheter tip and the tissue surface. A particular tip geometry such as a curved tip, tapered tip, or blunt tip may facilitate increased catheter tip-tissue contact for a curved, recessed, or flat tissue surface, respectively, which may increase burn densities and reduce ablation gap probabilities in the vicinity of the catheter tip for certain ablation points. However, the tip geometry may hinder catheter tip-tissue contact for tissue surfaces that are mismatched to the tip geometry, which may decrease burn densities and increase ablation gap probabilities in the vicinity of the catheter tip for these ablation points. Tip orientation may influence a symmetry or skewness of an ablation burn density distribution about a catheter tip-tissue contact point. For example, the ablation burn densities may be higher in a direction that the catheter tip is pointing, but may be lower in other directions. Applying insufficient catheter force at the tissue surface can decrease conduction of electrical energy from the catheter tip-tissue contact point and can result in a reduction in ablation burn densities and an increase in ablation gap probability.

Ablation device ablation tolerance variables can include ablation power, ablation duration, and impedance. In general, ablation burn densities may increase (and ablation gap probabilities may decrease) with increased ablation power, ablation duration, and impedance. However, applying excessive levels of power or ablating for prolonged duration can increase a risk of destroying tissue outside of the PVI region, resulting in adverse surgical complications. As described above with reference to FIG. 2, the LSI may be recorded as part of data from a completed ablation procedure that comprises a composite, dimensionless measure of several variables including ablation force, ablation power, and ablation duration. LSI data corresponding to each ablation site may be used to calculate ablation burn probabilities and/or ablation gap probabilities. A higher LSI, indicative of a larger lesion site, may increase ablation burn probabilities and reduce ablation gap probabilities. The Jump index (JI) may indicate a dimensionless distance between sequential ablation points. When the spatial distance between sequential ablation points is higher, JI may be increased. When the lesion size is increased, the spatial distance threshold above which the JI is increased (e.g., the threshold for a jump to be recorded) may be larger. The JI may thus indicate a measure of both lesion size and spatial vicinity of sequential ablation lesions, and may be one of a plurality of ablation tolerance variables that are utilized to calculate an ablation burn density or ablation gap probability distribution. Both the LSI and JI may be calculated at a patient interface module 120, application module and signal amplifier 130, or at the controller 178 of an EP ablation system, and recorded as part of the data associated with a completed EP ablation procedure.

The ablation device ablation tolerance variables may further include the type ablation technology or ablation energy. Ablation technologies may include resonant frequency, microwave, cryogenic, laser, and ultrasound. Each type of ablation technology may have a distinct ablation lesion distribution profiles. For example, resonant frequency energy may penetrate into certain tissues differently (more extensive or less extensive; more or less symmetrically about the catheter tip contact point; penetration may be deeper/broader or shallower/more focused; and the like) than other types of ablation technologies. Furthermore, each ablation technology type may have different parameters associated therewith, such as one or more of wavelength, amplitude, duration, pulse duration and frequency, temperature, focus diameter, and the like.

Examples of patient medical history ablation tolerance variables include a patient's age, health condition, and EP surgery history (including readmission frequency). Patient specific ablation tolerance variables may provide an indication of complications associated with a patient's medical history that may increase a likelihood of gaps between ablation burn points. For instance, if a patient has a history of frequent EP surgery readmissions, the calculated probability of gaps between ablation points may be increased because the risk of complications from surgery may be higher. Furthermore, the burn density may be reduced as the age of a patient increases due to the presence of scar tissue, reduced tissue regeneration ability, or other factors.

As described above, some of the data pertaining to ablation tolerance variables may be recorded and obtained from a completed EP ablation procedure. For instance, the catheter and the ablation variables (as listed in Table 1) may be available from recorded data from the completed EP ablation procedure. For example, information pertaining to the catheter type, size, force, tip orientation, and tip geometry, as well as the ablation power, duration and impedance associated with each ablation point may be recorded and stored in the system controller 178. In some examples, the ablation and catheter tolerance variables may be communicated to the controller 178 directly from the ablation device 184 and the force device 186 during the ablation procedure. Other variables such as the LSI and Jump Index may be calculated from a patient interface module 120 and/or an application module and signal amplifier 130 and communicated to the computer processor (controller 178). In other examples, the variables may include calculated variables. For example, controller 178 may calculate the LSI and the Jump Index.

In other examples, ablation tolerance variables may be input by the operator (e.g., operating physician, nurse, surgeon, technician, and the like). For instance, information from the patient's medical history such as prior EP ablation surgeries and readmission rate, and a patient's age, may be input into the controller 178 and taken into account when identifying the presence of gaps between ablation points. Other ablation tolerance variables such as those relating to tissue motion, anatomical topography, anatomical morphology, and operator experience may also be input by the operator. Furthermore, the operator may input different values for the ablation tolerance variables for different ablation points, depending on the conditions associated with each different ablation point. Further still, the operator may assign relative weights to each ablation tolerance variable, which can increase or decrease the relative contributions of each ablation tolerance variable to the ablation burn density and ablation gap probability calculations. In some examples, the operator may unevenly weight multiple ablation tolerance variables while in other examples the operator may evenly weight multiple ablation tolerance variables. In this way, the algorithm for calculating the ablation burn density and ablation gap probability, and for identifying ablation gaps can be more customizable and flexible, depending on the nature of the surgery, the patient's history, the operator expertise, the ablation and catheter devices used, and the like. In other words, the operator can have increased control or can more reliably prescribe the way ablation gaps are identified.

Returning to FIG. 4, it also illustrates overlap regions 424, 434, and 444 between sequential ablation points. Namely, overlap region 424 is formed from the overlap of ablation points 420 and 430; overlap region 434 is formed from the overlap of ablation points 430 and 440; and overlap region 444 is formed from the overlap of ablation points 440 and 450. As shown in FIG. 4, the overlap regions 424, 434, and 444 are represented by a shading value that is a composite of the ablation points from which they are formed. For example, overlap region 424 is slightly darker than the regions of ablation points 420 and 430 immediately adjacent to the borders of overlap region 424. The size of the overlap regions may depend on the size of the sequential ablation points, and their spatial proximity. Although the overlap regions 424, 434, and 444 are formed from two overlapping sequential ablation points, in other examples, overlap regions may be formed from more than two overlapping sequential ablation points. Furthermore, the ablation points may be represented by 3D ablation distributions. As such the overlap regions between sequential ablation points may also be 3D overlap regions between two or more sequential ablation points. These overlap regions may also be overlaid on to a 2D or 3D anatomical model 300 and displayed on an operator display 174 of the EP ablation system 100.

In the case where ablation points 420 and 430 represent ablation burn density distributions, the overlap region 424 may thus represent a composite ablation burn density distribution. The composite burn density map may be computed by an operator-defined transfer function of the various ablation tolerance variables and parameters, and the various input ablation burn density distributions and parameters associated therewith. As a non-limiting example, ablation burn density of the overlap region 424 may be calculated by summing the burn densities of the portions of the ablation points 420 and 430 forming the overlap region 424. In another example, the ablation burn density of the overlap region 424 may be calculated by averaging the burn densities of the portions of the ablation points 420 and 430 forming the overlap region 424. In another example, the ablation burn density of the overlap region 424 may be calculated by taking a weighted average of the burn densities of the portions of the ablation points 420 and 430 forming the overlap region 424. The weighting of the contributing ablation point burn densities to the overlap region 424 may be determined according to the relative uncertainty or tolerance of each ablation point 420 and 430. For instance, the weighting may be higher for ablation points with lower uncertainties, whereas the weighting may be lower for ablation points with higher uncertainties. As such, the contributions to ablation gap probabilities from overlapping ablation points may be accounted for when predicting or identifying ablation gaps. In contrast, conventional methods for representing ablation points as homogeneous distributions (e.g., ablation points 330 and 340) simplistically assume that overlapping ablation points preclude the existence of ablation gaps therebetween. As a result, identifying ablation gaps can be more reliably identified (thereby reducing EP ablation readmission rates) when representing ablation points as distributions relative to conventional methods of representing ablation points as homogeneous distributions. In other examples, methods of computing the composite ablation burn density distributions may involve (but are not limited to) polynomial, exponential, and spline transformations.

Turning now to FIGS. 6 and 7, they illustrate additional example methods of calculating ablation gap probabilities between pairs of sequential ablation points 602 and 604, and 702 and 704. For illustration purposes, the ablation points 602, 604, 702, and 704 are represented by discrete distributions (e.g., discrete ablation burn density distributions and/or discrete ablation gap probability distributions). The annular regions 610, 612, 614, 616, 618, and 620 represent regions of increasing ablation burn density from an outer perimeter of the ablation point 602 towards a center region 622 of the ablation point 602. Similarly, annular regions 640, 642, 644, 646, and 648 represent regions of increasing ablation burn density from an outer perimeter of the ablation point 604 towards a center region 650 of the ablation point 604. As shown by the relative sizes in the ablation point perimeters, the apparent size of the ablation point 604 is smaller than the ablation point 602. The spatial proximity of ablation points 602 and 604 form a series of overlap regions 628, 630, 632, and 634 therebetween comprising a composite of each of the overlapping annular regions. For example, overlap region 628 may represent a composite ablation burn density formed from the ablation burn density of annular regions 612 and 640; overlap region 630 may represent a composite ablation burn density formed from the ablation burn density of annular regions 610 and 640; overlap region 632 may represent a composite ablation burn density formed from the ablation burn density of annular regions 610 and 642; and overlap region 634 may represent a composite ablation burn density formed from the ablation burn density of annular regions 610 and 644. As analogously described with reference to FIG. 4 for the case of ablation points represented as continuous distributions, ablation burn densities and/or ablation gap probabilities within the overlap regions 628, 630, 632, and 634 may be calculated by averaging (e.g. summing, weighted average, unweighted average, and the like) the individual distributions from which they are formed. For instance, the ablation burn density of overlap region 630 may be calculated from a weighted average of the ablation burn densities of annular regions 610 and 640. Furthermore, for the case where the ablation point 604 has a lower associated tolerance (or uncertainty) than that of ablation point 602, the weighting or contribution of the ablation burn density of annular region 640 may be higher than that or annular region 610 towards the calculation of the ablation burn density of overlap region 630.

Turning now to FIG. 7, it illustrates an analogous method for the pair of ablation points 702 and 704. The annular regions 710, 712, 714, 716, 718, and 620 represent regions of increasing ablation burn density from an outer perimeter of the ablation point 702 towards a center region 722 of the ablation point 702. Similarly, annular regions 740, 742, 744, 746, and 748 represent regions of increasing ablation burn density from an outer perimeter of the ablation point 704 towards a center region 750 of the ablation point 704. As shown by the relative sizes in the ablation point perimeters, the apparent size of the ablation point 704 is smaller than the ablation point 702. The spatial proximity of ablation points 702 and 704 form a series of overlap regions within an area 730 (indicated by the dotted ellipse) including overlap regions 728, 732, and 734 therebetween comprising a composite of each of the overlapping annular regions.

FIGS. 6 and 7 further illustrate how representation of the ablation points as discrete or continuous distributions rather than homogeneous (uniform) distributions may be advantageous for reducing false positive and false negative errors in identifying gaps between sequential ablation points. False positive errors may refer to identifying gaps in EP ablation points where there are none; false negative errors may refer to failure to identify gaps in EP ablation points where there are gaps. For example, for the case where the sequential ablation points 602 and 604 are conventionally represented as homogeneous (solid) distributions whose perimeters correspond to the perimeters of annuli 610 and 640, an ablation gap between the ablation points 602 and 604 would not be identified because they overlap. However by accounting for the non-homogenous distribution of ablation burn densities (and ablation gap probabilities) for each ablation point 602 and 604, ablation gaps may be identified between the ablation points 602 and 604 if any of the ablation burn densities of overlap regions 628, 630, 632, and 634 is lower than a threshold ablation burn density. The threshold ablation burn density may be selected to correspond to an ablation burn density below which the likelihood for an ablation gap is high. Thus, representing the ablation points as non-homogeneous distributions can aid in avoiding false negative (e.g. Type II) errors in identifying ablation gaps.

Similarly, for the case where the sequential ablation points 702 and 704 are conventionally represented as homogeneous (solid) distributions whose perimeters correspond to the perimeters of annuli 720 and 748, an ablation gap between the ablation points 702 and 704 may always be identified because the perimeters of regions 720 and 748 do not overlap. However by accounting for the non-homogenous distribution of ablation burn densities (and ablation gap probabilities) for each ablation point 702 and 704, the calculated ablation burn densities may actually extend beyond the perimeters of the homogeneous distributions, and the ablation burn densities of these extended regions of the ablation points 702 and 704 may overlap, as shown in FIG. 7. Furthermore, no ablation gaps may be identified between the ablation points 702 and 704 if any of the ablation burn densities of overlap regions within 730 (e.g., overlap regions 628, 632, and 634) are higher than a threshold ablation burn density. The threshold ablation burn density may be selected to correspond to an ablation burn density below which the likelihood for an ablation gap is high. Thus, representing the ablation points as non-homogeneous distributions can aid in avoiding false positive (e.g. Type I) errors in identifying ablation gaps.

Turning now to FIG. 5, it illustrates a flow chart for a method 500 of identifying gaps between ablation points for an EP ablation system. The method 500 may be executed as instructions residing on a computer controller 178 of an EP ablation system. The method may include receiving inputs at the controller 178 from various sensors and devices, as described with reference to FIG. 1 above, and may further include outputting signals to an operator display 174 of the EP ablation system. Furthermore, method 500 may be executed to non-invasively identify ablation gaps, without introducing additional instruments into a patient's body. Further still, method 500 may advantageously be executed following a completed EP ablation procedure, prior to patient discharge. For example, method 500 may be used to identify ablation gaps resulting from the EP ablation procedure, and prior to the patient being discharged or disconnected from the EP ablation system, follow-up EP ablation may be carried out by the operator at the identified ablation gaps in order to remove the identified ablation gaps. In this way, a readmission rate of EP ablation may be reduced, thereby decreasing healthcare costs, increasing patient satisfaction, and reducing a risk of EP ablation complications.

Method 500 begins at 510 where ablation points recorded from a completed EP procedure are obtained. The ablation points may include data associated with lesion sites such as lesion location, and catheter and ablation device data such as ablation power, ablation duration, catheter tip size and orientation, and the like. The ablation point data may each include associated tolerances indicating a level of precision or uncertainty associated with the data. Some examples of data recorded from a completed ablation procedure are illustrated in FIG. 2. Next, method 500 continues at 520 where the ablation points are digitally mapped to an anatomical model. The anatomical model may include a 2D and/or 3D anatomical model, as shown in FIG. 3, and digitally mapping the ablation points may include 2D mapping the ablation points onto a 2D anatomical model and 3D mapping the ablation points onto a 3D anatomical model. The mapping process may have an associated tolerance or level of uncertainty for positioning the ablation points accurately. Furthermore, there may be uncertainties associated with fidelity of the anatomical model to a patient's tissue. For example, ablation points are typically mapped to anatomical models with a navigation tolerance of ±1 to 4 mm at each ablation point.

Next at 530, the method 500 determines values for a plurality of ablation tolerance variables to be utilized for calculating ablation burn density distributions and ablation gap probabilities associated with each ablation point. As described above with reference to Table 1, examples of the ablation tolerance variables can include tissue motion, operator experience, anatomical morphology, anatomical topography, catheter, ablation device, and patient related ablation tolerance variables. In some examples, ablation tolerance variable values for each ablation point can be obtained from the recorded data from the completed ablation procedure, such as for catheter and ablation device ablation tolerance variables. In other cases, the ablation tolerance variable values may be calculated at a controller 178 or other module within the EP ablation system. Furthermore, method 500 may also prompt an operator to input ablation tolerance variable values for each ablation point. For example, the operator experience and patient related ablation tolerance variables may be input by an operating physician. Alternately, the patient related ablation tolerance variables may be stored on an external computer medical records system in communication with the controller 178. As further examples, the anatomical morphology and anatomical topology ablation tolerance variables may be input by an operator, and/or may be calculated using anatomical data from the 2D or 3D anatomical model. The anatomical model may be pre-stored on the controller 178 or another module of the EP ablation system 100 such as the patient interface module 120 and the application module and signal amplifier 130. At step 530, the operator may further assign weighting values to one or more of the ablation tolerance variables in order to adjust the relative contribution of those one or more ablation tolerance variables to calculating the ablation burn densities and ablation gap probability distributions. In some examples, the controller 178 may present a comprehensive list of ablation tolerance variables to the operator by way of the operator display 174; then, the operator can input values and assign weights to each ablation tolerance variable on which calculations of the ablation burn density and ablation gap probability distributions are to be based. Furthermore, by assigning weights to each ablation tolerance variable, the operator can select the ablation tolerance variables on which the calculation of ablation burn density probabilities and ablation gap probabilities can be based. The weighting of ablation tolerance variables may vary for different ablation points. As one example, for the case of an ablation point located at a site associated with highly irregular anatomical morphology and highly irregular anatomical topology, the weighting may be selected such that the uncertainty is higher and the ablation gap probability is higher. In this way, gaps between ablation points may be located at regions of higher uncertainty. In other examples, by setting their respective weighting to zero, the influence of certain ablation tolerance variables in calculating ablation burn density probabilities and ablation gap probabilities can be removed. In other words, vectors of weighted ablation tolerance variables are applied at each ablation point in order to compute ablation burn density distributions and ablation gap probability distributions.

Next, at 540, method 500 continues by calculating the ablation gap probability distributions and/or ablation burn density distributions for each ablation point based on the provided set of ablation tolerance variables and associated weights from 530. Calculating the ablation gap probability distributions and/or the ablation burn density distributions can include determining the type of distribution for representing the ablation burn density and ablation gap probability distributions. For instance, as described above, a Gaussian (normal) distribution, or other types of statistical distributions can be used. In the case of a Gaussian distribution, the method 500 may, based on the ablation tolerance variables and recorded data from the completed ablation procedure, estimate parameters for specifying the Gaussian distribution, such as the mean and standard deviation, at each ablation point. In the case of other types of statistical distributions, values of other parameters specifying the statistical distributions may be calculated. In some examples, the method may allow for an operator to specify different statistical distributions corresponding to the ablation burn density and ablation gap probability distributions for different ablation points. For example, a first ablation point may have a Gaussian ablation burn density distribution (2D or 3D); while a second ablation point may have a non-Gaussian ablation burn density distribution (2D or 3D). Examples of other types of statistical distributions are described above with reference to FIGS. 4, 6, and 7.

At 550, method 500 continues by overlaying the ablation burn density and/or ablation gap probability distributions onto the anatomical model. As described above the ablation burn density and ablation gap probability distributions may include 2D and 3D distributions. Furthermore, the anatomical model on which the ablation burn density and ablation gap probability distributions are overlaid may include 2D and 3D anatomical models. Overlaying the ablation burn density and/or ablation gap probability distributions onto the anatomical model may further include calculating ablation burn density and ablation gap probability values in overlap regions for two or more sequential ablation points, as discussed above with reference to FIGS. 4, 6, and 7. The ablation burn density and ablation gap probability values in overlap regions may be calculated by combining contributions from the plurality of overlapping ablation points. Combining contributions may refer to summing, averaging, weight-averaging, or another method of accounting for the combined contributions.

Next, at 560, method 500 evaluates the gap criteria at each ablation point in order to identify or predict gaps between ablation points. In one example, method 500 may identify gaps between ablation points at regions where the ablation gap probability is greater than a threshold ablation gap probability. Similarly, method 500 may identify gaps between ablation points at regions where the ablation burn density is less than a threshold ablation burn density. Furthermore, identifying an ablation gap criteria may further include an additional criterion evaluating if the region where the ablation gap probability is greater than a threshold ablation gap probability or where the ablation burn density is less than a threshold ablation burn density is larger than a threshold size. For a two-dimensional anatomical model, the threshold size may correspond to a threshold area, whereas for a three-dimensional model, the threshold size may correspond to a threshold swept out volume, or a threshold projected area. In other examples, the threshold size may correspond to a dimension (one-, two-, or three-dimensional) corresponding to a threshold tolerance of the anatomical model, mapping process, and or other dimensional tolerances. In other examples, multiple threshold size criterion may be evaluated, and the ablation gap may be identified as a marginal gap or an isolated gap, depending on the threshold size criteria satisfied. In the case of a marginal gap, an operator may or may not choose to carry out a follow-up EP ablation to remove the marginal gap since the risk of further complications resulting from the follow-up EP ablation may exceed the risk of complications resulting from the marginal gap. In the case of an isolated gap, an operator may choose to carry out a follow-up EP ablation to remove the isolated gap to reduce a risk of unintended electrical leakage relative to a PVI barrier, or a conductive zone being created disrupting a long continuous ablation burn. For the case of EP ablation for treating arrhythmia, an operator can thus reduce a risk of unintended propagation of electrical signals in cardiac tissue resulting in formation of an arrhythmic event. Furthermore, the identification of gaps, both marginal and isolated, may provide a potential metric (e.g., number of marginal and isolated gaps) by which an EP ablation procedure can be measured for reliably predicting patient readmission.

If at 560, the gap criteria is not satisfied at any of the ablation points, method 500 ends. If the gap criteria is satisfied, method 500 continues at 570 where an ablation gap is indicated on the anatomical model at the operator display 174. Indicating an ablation gap may include a visual and/or audio marker. Indicating the ablation gap may further include recommendations for follow-up ablation procedures at each identified ablation gap prior to discharging the patient. For example, in response to the indication of ablation gaps at 570, method 500 may recommend further EP ablation at the identified ablation gaps, prior to patient discharge and while the patient is still connected to the EP ablation system. The operator may then more conveniently and expeditiously conduct the follow-up EP ablation while avoiding costs associated with readmission. Furthermore, timely follow-up EP ablation may reduce a risk of complications associated with edema or scarring, or other health risks associated with the surgery. After 570, method 500 ends.

In this way, methods and systems for non-invasively identify ablation gaps may be executed, without introducing additional instruments into a patient's body. Further still, the methods and systems described herein may advantageously be executed following a completed EP ablation procedure, and prior to patient discharge. For example, method 500 may be used to identify ablation gaps resulting from the EP ablation procedure, and prior to the patient being discharged or disconnected from the EP ablation system, follow-up EP ablation may be carried out by the operator at the identified ablation gaps in order to remove the identified ablation gaps. Furthermore, by more accurately and expeditiously identifying gaps between ablation points, EP ablation procedure times can be decreased, thereby increasing clinic throughput, while reducing patient risk. In this way, a readmission rate of EP ablation may be reduced, thereby decreasing healthcare costs, increasing patient satisfaction, and reducing a risk of EP ablation complications. Reducing a risk of EP ablation readmission may advantageously reduce stroke risk, reduce patient drug costs, increase patient quality of life, reduce long term heart fibrosis, and reduce a risk of sudden cardiac death. Furthermore, by representing ablation points using calculated ablation burn density distributions and ablation gap probabilities, the accuracy of identifying ablation gaps may be increased as compared to conventional methods. Further still, by basing the calculation of ablation burn density and ablation gap probability distributions on a plurality of ablation tolerance variables, uncertainties in the EP ablation system and procedures can be more comprehensively accounted for. Further still, by allowing the ablation tolerance variables to be input by the operator and also weighted by the operator, the method of identifying ablation gaps is rendered more flexible and easily retrofitted to existing EP ablation systems and can be more readily adapted by experienced and non-experienced physicians. Further still, by accounting for operator experience variation in the calculation of ablation burn densities and ablation gap probabilities, operator to operator variability associated with conducting EP ablation may be reduced. Further still, by representing ablation points as 2D or 3D distributions of ablation burn densities and ablation gap probabilities, the risk of misidentifying or failing to identify a gap between ablation points can be reduced.

In this manner, a method of identifying gaps between electrophysiology ablation points may comprise: obtaining a plurality of ablation points recorded from a completed electrophysiology ablation procedure; digitally mapping the plurality of ablation points to an anatomical model corresponding to the completed electrophysiology ablation procedure; calculating ablation gap probability distributions for each of the plurality of ablation points based on ablation tolerance variables associated with each of the plurality of ablation points; and overlaying the ablation gap probability distributions on to the digitally mapped plurality of ablation points on the anatomical model. Obtaining the plurality of ablation points, digitally mapping the plurality of ablation points, calculating the ablation gap probability distributions, and overlaying the ablation gap probability distributions may each be performed non-invasively, without introducing instruments into a patient's body. Furthermore, the method may comprise indicating ablation gaps in the overlaid ablation gap probability distributions when an ablation gap probability increases above a threshold ablation gap probability. In some examples, determining the ablation gap probability may include combining overlapping contributions of ablation gap probability distributions associated with two of the plurality of ablation points. Furthermore, the ablation tolerance variables may include an anatomical topography variable, an ablation gap probability for an ablation point increasing when the anatomical topography variable indicates a more irregular anatomical topography at the ablation point. Further still, the ablation tolerance variables may include an operator experience variable, an ablation gap probability for the ablation point increasing when the operator experience variable indicates a lower operator experience. The ablation tolerance variables upon which the calculated ablation gap probability distributions may be unevenly weighted, and the calculated ablation gap probability distributions at two of the plurality of ablation points may be unequal.

In another embodiment, a method of identifying gaps between electrophysiology ablation points may comprise: obtaining a plurality of ablation points recorded from a completed electrophysiology ablation procedure; digitally mapping the plurality of ablation points on to an anatomical model corresponding to the completed electrophysiology ablation procedure; calculating ablation burn probability distributions for each of the plurality of ablation points based on ablation tolerance variables associated with each of the plurality of ablation points; and overlaying the ablation burn probability distributions on to the digitally mapped plurality of ablation points on the anatomical model. The method may further comprise indicating ablation gaps in the overlaid ablation burn probability distributions when the ablation burn probability decreases below a threshold ablation burn probability. In some examples, calculating ablation burn probability distributions for each of the plurality of ablation points may comprise determining parameters defining the ablation probability distributions at each of the plurality of ablation points based on the ablation tolerance variables. Furthermore, calculating ablation burn probability distributions for each of the plurality of ablation points may comprise assigning weights to the ablation tolerance variables, wherein the weights determine the relative contribution of each of the ablation tolerance variables to determining the parameters defining the ablation probability distributions. Assigning weights to the ablation tolerance variables may include assigning user-input weights, and calculating the ablation burn probability distributions can comprise calculating a Gaussian ablation burn probability distribution, including calculating a mean and a standard deviation of the Gaussian ablation burn probability distribution based on the ablation tolerance variables.

In a further embodiment, an electrophysiology ablation system may comprise, an operator display, and a controller electrically coupled to the operator display, the controller including executable instructions thereon to: obtain a plurality of ablation points recorded from a completed electrophysiology ablation procedure; digitally map the plurality of ablation points on to an anatomical model corresponding to the completed electrophysiology ablation procedure; calculate ablation gap probability distributions for each of the plurality of ablation points based on ablation tolerance variables associated with each of the plurality of ablation points; overlay the ablation gap probability distributions on to the digitally mapped plurality of ablation points on the anatomical model; and display the ablation gap probability distributions overlaid on to the digitally mapped plurality of ablation points on the anatomical model on the operator display. In some examples, the executable instructions may include determining an ablation gap probability at a first position between two of the plurality of ablation points by combining overlapping ablation gap probability distributions associated with the two ablation points. The executable instructions may further include, in response to an ablation gap probability at the first position between two ablation burn points being greater than a threshold probability, displaying a gap indication on the operator display at the first position. The ablation tolerance variables may include a tissue motion variable, wherein the ablation gap probability corresponding to an ablation point increases when the tissue motion variable indicates a higher time-varying rate of change in position of the ablation point. Furthermore, the ablation tolerance variables may include a patient history variable, wherein the ablation gap probability corresponding to the ablation point increases when the patient history variable indicates a patient history associated with a higher surgery complication risk. The executable instructions to overlay the ablation gap probability distributions on to the digitally mapped plurality of ablation points on the anatomical model may include overlaying three-dimensional ablation gap probability distributions on to the digital mapped plurality of ablation points on a three-dimensional anatomical model.

It is to be understood that the description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to those of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

Additionally, the term pixel is used throughout the specification and should be interpreted to include one or more pixel. The term pixel is not restricted by any number because of the use of singular or multiple form.

This written description uses examples to disclose several embodiments of the inventive subject matter and also to enable any person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described systems and methods, without departing from the spirit and scope of the inventive subject matter herein involved, it is intended that all of the subject matter of the above description or shown in the accompanying drawings shall be interpreted merely as examples illustrating the inventive concept herein and shall not be construed as limiting the inventive subject matter.

This written description uses examples to disclose the invention, including the best mode, and also to enable a person of ordinary skill in the relevant art to practice the invention, including making and using any devices or systems and performing any incorporated methods. The patentable scope of the invention is defined by the claims and may include other examples that occur to those of ordinary skill in the art. Such other examples are intended to be within the scope of the claims if they have structural elements that do not differ from the literal language of the claims or if they include equivalent structural elements with insubstantial differences from the literal languages of the claims.

The invention claimed is:

1. A method of identifying gaps between electrophysiology ablation points, comprising:
   obtaining a plurality of ablation points recorded from a completed electrophysiology ablation procedure;
   digitally mapping the plurality of ablation points to an anatomical model corresponding to the completed electrophysiology ablation procedure;
   calculating ablation gap probability distributions for each of the plurality of ablation points based on ablation tolerance variables associated with each of the plurality of ablation points; and
   overlaying the ablation gap probability distributions on to the digitally mapped plurality of ablation points on the anatomical model;
   wherein obtaining the plurality of ablation points, digitally mapping the plurality of ablation points, calculating the ablation gap probability distributions, and overlaying the ablation gap probability distributions are each performed non-invasively, without introducing instruments into a patient's body.

2. The method of claim 1, further comprising indicating ablation gaps in the overlaid ablation gap probability distributions when an ablation gap probability increases above a threshold ablation gap probability.

3. The method of claim 2, wherein determining the ablation gap probability includes combining overlapping contributions of ablation gap probability distributions associated with two of the plurality of ablation points.

4. The method of claim 3, wherein the ablation tolerance variables include an anatomical topography variable, wherein an ablation gap probability for an ablation point increases when the anatomical topography variable indicates a more irregular anatomical topography at the ablation point.

5. The method of claim 4, wherein the ablation tolerance variables include an operator experience variable, wherein an ablation gap probability for the ablation point increases when the operator experience variable indicates a lower operator experience.

6. The method of claim 5, wherein the ablation tolerance variables upon which the calculated ablation gap probability distributions are unevenly weighted.

7. The method of claim 6, wherein the calculated ablation gap probability distributions at two of the plurality of ablation points are unequal.

8. The method of claim 1, further comprising indicating ablation gaps in the overlaid ablation burn probability distributions when the ablation burn probability decreases below a threshold ablation burn probability.

9. The method of claim 8, wherein calculating ablation burn probability distributions for each of the plurality of ablation points comprises determining parameters defining the ablation probability distributions at each of the plurality of ablation points based on the ablation tolerance variables.

10. The method of claim 9, wherein calculating ablation burn probability distributions for each of the plurality of ablation points comprises assigning weights to the ablation tolerance variables, wherein the weights determine the relative contribution of each of the ablation tolerance variables to determining the parameters defining the ablation probability distributions.

11. The method of claim 10, wherein assigning weights to the ablation tolerance variables comprises assigning user-input weights.

12. The method of claim 11, wherein calculating the ablation burn probability distributions comprises calculating a Gaussian ablation burn probability distribution, including calculating a mean and a standard deviation of the Gaussian ablation burn probability distribution based on the ablation tolerance variables.

13. An electrophysiology ablation system, comprising:
   an operator display, and
   a controller electrically coupled to the operator display, the controller including executable instructions thereon to:
   obtain a plurality of ablation points recorded from a completed electrophysiology ablation procedure;
   digitally map the plurality of ablation points on to an anatomical model corresponding to the completed electrophysiology ablation procedure;
   calculate ablation gap probability distributions for each of the plurality of ablation points based on ablation tolerance variables associated with each of the plurality of ablation points;

overlay the ablation gap probability distributions on to the digitally mapped plurality of ablation points on the anatomical model; and display the ablation gap probability distributions overlaid on to the digitally mapped plurality of ablation points on the anatomical model on the operator display;

wherein the controller executes the instructions to obtain the plurality of ablation points, digitally map the plurality of ablation points, calculate the ablation gap probability distributions, and overlay the ablation gap probability distributions are each performed non-invasively, without introducing instruments into a patient's body.

14. The electrophysiology ablation system of claim 13, wherein the executable instructions further comprise, determining an ablation gap probability at a first position between two of the plurality of ablation points by combining overlapping ablation gap probability distributions associated with the two ablation points.

15. The electrophysiology ablation system of claim 14, wherein the executable instructions further comprise, in response to an ablation gap probability at the first position between two ablation burn points being greater than a threshold probability, displaying a gap indication on the operator display at the first position.

16. The electrophysiology ablation system of claim 15, wherein the ablation tolerance variables comprises a tissue motion variable, wherein the ablation gap probability corresponding to an ablation point increases when the tissue motion variable indicates a higher time-varying rate of change in position of the ablation point.

17. The electrophysiology ablation system of claim 16, wherein the ablation tolerance variables comprises n patient history variable, wherein the ablation gap probability corresponding to the ablation point increases when the patient history variable indicates a patient history associated with a higher surgery complication risk.

18. The electrophysiology ablation system of claim 17, wherein the executable instructions to overlay the ablation gap probability distributions on to the digitally mapped plurality of ablation points on the anatomical model include overlaying three-dimensional ablation gap probability distributions on to the digital mapped plurality of ablation points on a three-dimensional anatomical model.

\* \* \* \* \*